United States Patent [19]

Friebe et al.

[11] 4,428,955
[45] Jan. 31, 1984

[54] BENZOPYRAN COMPOUNDS, PHARMACEUTICAL COMPOSITIONS CONTAINING THEM AND METHODS OF USE

[75] Inventors: Walter-Gunar Friebe, Darmstadt; Wolfgang Kampe, Heddesheim; Egon Röesch, Mannheim; Otto-Henning Wilhelms, Weinheim-Rittenweier, all of Fed. Rep. of Germany

[73] Assignee: Boehringer Mannheim GmbH, Mannheim, Fed. Rep. of Germany

[21] Appl. No.: 372,415

[22] Filed: Apr. 27, 1982

[30] Foreign Application Priority Data

May 2, 1981 [DE] Fed. Rep. of Germany ....... 3117389

[51] Int. Cl.³ .................. A61K 31/445; C07D 405/12; C07D 405/14
[52] U.S. Cl. .................................... 424/267; 546/193; 546/196
[58] Field of Search .................. 546/196, 193; 424/267

[56] References Cited

U.S. PATENT DOCUMENTS 3,046,275  7/1962  Kohlstaedt et al. ................ 546/196
4,330,549  5/1982  Friebe et al. ........................ 546/196

Primary Examiner—Robert T. Bond
Attorney, Agent, or Firm—Felfe & Lynch

[57] ABSTRACT

The present invention provides benzopyranyl ethers of the general formula:

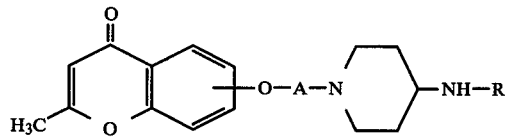

wherein A is an alkylene radical containing 2 to 4 carbon atoms and R is a hydrogen atom or an acyl radical; as well as the salts thereof with pharmacologically acceptable acids.

The present invention also provides processes for the preparation of these compounds and pharmaceutical compositions containing them. Furthermore, the present invention is concerned with the use of these compounds for treating allergic diseases.

17 Claims, No Drawings

BENZOPYRAN COMPOUNDS, PHARMACEUTICAL COMPOSITIONS CONTAINING THEM AND METHODS OF USE

This invention relates to new benzopyran compounds, more specifically benzopyranyl ether compounds, and to a process for their preparation. In additional aspect the invention relates to pharmaceutical compositions containing such compounds and to therapeutic methods utilizing such compounds.

The new compounds, as well as their pharmacologically acceptable salts, even when administered orally in low doses, have an inhibiting action on anaphylactic reactions of the skin and bronchial system. A weak antioedematous effect has also been observed. At the same time, they also antagonise mediators liberated by allergens, for example histamine.

Compounds of a similar constitution have been disclosed in Federal Republic of Germany Patent No. 29 01 336. We have now found, however, that compounds which, in place of a coumarine residue, contain a 2-methylchromone residue, also display an outstanding anti-allergic action.

Thus, according to the present invention, there are provided benzopyran derivatives of the general formula:

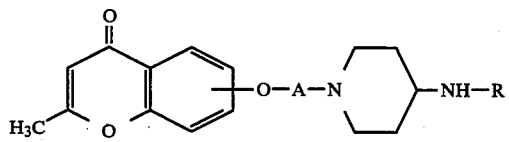 (I)

wherein A is an alkylene radical containing 2 to 4 carbon atoms and R is a hydrogen atom or an acyl radical, as well as the salts thereof with pharmacologically acceptable acids.

The present invention also provides pharmaceutical compositions containing at least one of the compounds of general formula (I) and is also concerned with the use of compounds of general formula (I) for the preparation of such compositions.

The alkylene radicals A can be straight-chained or branched, the preferred alkylene radical being the trimethylene radical.

The acyl radicals R can be lower alkanoyl radicals containing up to 5 carbon atoms which are optionally substituted by halogen or aryl, lower alkenoyl radicals containing 3 to 6 carbon atoms, which are optionally substituted by aryl which, in turn, optionally carries one or more substituents, for example an optionally substituted cinnamoyl radical, or carbocyclic or heterocyclic aroyl radicals, which can optionally be substituted one or more times by halogen, hydroxyl, lower alkyl, lower alkoxy, lower alkoxycarbonyl, lower alkanoyloxy, carboxyl, nitro, amino, lowr alkanoylamino, nitrilo, trifluoromethyl, carbamoyl, lower alkylthio, lower alkylsulphinyl, lower alkylsulphonyl, lower alkanoyl, aroyl, hydroxy lower alkyl or lower alkoxy lower alkyl.

The lower alkyl radicals in the above-mentioned groups each contain up to 6 and preferably up to 4 carbon atoms, the radicals being straight-chained or branched, the methyl radical being preferred. Heterocyclic aroyl radicals include, for example, the furancarbonyl, the thiophenecarbonyl and the pyridinecarbonyl radicals and carbocyclic aroyl radicals include, for example, the benzoyl or naphthoyl radicals.

Furthermore, R can represent the acid residue of a carbocyclic or heterocyclic carboxylic acid, the cycloalkyl radical preferably being a cyclopropyl, cyclobutyl, cyclopentyl, cyclohexyl or cycloheptyl radical and the heterocycle preferably being a tetrahydrofuran or tetrahydrothiophene radical.

Furthermore, when R is an acyl radical, it can also be the acid residue of a sulphonic acid, for example of benzenesulphonic acid or methanesulphonic acid.

The expression "aryl" in the definitions of the substituents R preferably means a phenyl or naphthyl radical. Substituents possibly present in the aryl radicals include hydroxyl, halogen and alkyl and alkoxy containing up to 6 carbon atoms.

The halogen atoms can be fluorine, chlorine or bromine atoms.

Apart from the compounds mentioned hereinafter in the specific Examples, the present invention also includes all compounds which display every possible combination of the substituents mentioned in the Examples.

The ether substituent of the benzopyran ring can be in the 5-, 6- or 7-position, the 7-position being preferred.

The process according to the present invention for the preparation of the compounds of general formula (I) is characterised in that a compound of the general formula:

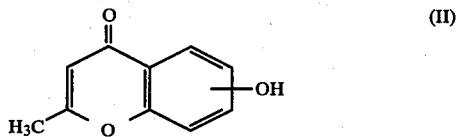 (II)

is reacted in per se known manner with a compound of the general formula:

X—A—Y (III), in which X and Y are reactive residues and A has the same meaning as above, and with a compound of the general formula:

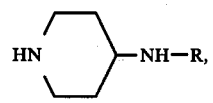 (IV)

in which R has the same meaning as above, whereafter, if desired, the group R is converted into a different group R with the above-given definition, and the reaction product obtained is, if desired, converted into a pharmacologically acceptable salt.

The reactive residues X and Y in the compounds of general formula (III) can be chlorine or bromine atoms or mesyloxy or tosyloxy radicals.

The process according to the present invention is preferably carried out, for example, by first condensing a compound of general formula (III) with a compound of general formula (IV) and the reaction product obtained isolated. This intermediate is then reacted with a compound of general formula (II). The reaction is preferably carried out in an alkaline medium, for example in a lower alcohol, such as isopropyl alcohol, in the presence of sodium isopropanolate or in dimethylformamide in the presence of potassium carbonate.

According to another variant, a compound of general formula (II) is first reacted with a compound of general formula (III). Subsequently, the reaction mixture obtained is reacted with a compound of general formula (IV) to give the desired end product of general formula (I).

A subsequent conversion of a group R in a compound of general formula (I) into a different group R can take place, for example, by acylation of a compound of general formula (I), in which R is a hydrogen atom, with a compound of the general formula R.Z, in which Z is a reactive group. Compounds of general formula (I), in which R is a hydrogen atom, thus represent valuable intermediates for the preparation of other compounds of general formula (I). Reactive residues Z can be all residues which are used in peptide chemistry for the activation of carboxylic acids, for example halogen atoms, the azido group and alkoxy, aryloxy and acyloxy radicals.

According to another possibility for the subsequent conversion of the group R in a compound of general formula (I), one or more substituents in the acyl radical R are converted in conventional manner, for example by esterification, saponification, reduction, alkylation, acylation, hydrogenolysis, oxidation, amidation or elimination, into one or more other substituents in the acyl radical R.

The starting materials of general formulae (II), (III) and (IV) are known from the literature or can be prepared in a manner analogous to that described in the literature.

The pharmacologically acceptable salts are obtained in the usual manner, for example by neutralisation of the compounds of general formula (I) with nontoxic inorganic or organic acids, for example hydrochloric acid, sulphuric acid, phosphoric acid, hydrobromic acid, acetic acid, lactic acid, citric acid, malic acid, salicylic acid, malonic acid, maleic acid or succinic acid.

For the preparation of pharmaceutical compositions, the compounds of general formula (I) are mixed in known manner with appropriate pharmaceutical carrier materials, aroma, flavouring and colouring materials and formed, for example, into tablets or dragees or, with the addition of appropriate adjuvants, suspended or dissolved in water or an oil, for example olive oil.

The compounds of general formula (I) can be administered orally or parenterally in liquid or solid form. As injection medium, it is preferable to use water which contains the stabilising agents, solubilising agents and/or buffers which are conventional for injection solutions. Additives of this kind include, for example, tartrate and borate buffers, ethanol, dimethyl sulphoxide, complex formers (such as ethylenediamine-tetraacetic acid), high molecular weight polymers (such as liquid polyethylene oxide) for viscosity regulation or polyethylene derivatives or sorbite anhydrides.

Solid carrier materials include, for example, starch, lactose, mannitol, methyl cellulose, talc, highly dispersed silicic acid and high molecular weight polymers (such as polyethylene glycols).

Compositions suitable for oral administration can, if desired, contain flavouring and sweetening agents. For external administration, the compounds of general formula (I) according to the present invention can also be used in the form of powders or salves. For this purpose, they are mixed, for example, with powdered, physiologically compatible diluents or conventional salve bases.

The dosage administered depends upon the age, state of health and weight of the recipient, the extent of the disease, the nature of other treatments possibly carried out at the same time, the frequency of the treatment and the nature of the desired effect. Usually, the daily dosage of the active compound amounts to 0.1 to 50 mg./kg. of body weight. Normally, 0.5 to 40 and preferably 1.0 to 20 mg./kg./day in one or more administrations per day are effective for obtaining the desired results.

Apart from the compounds mentioned in the following Examples, the following compounds are also preferred according to the present invention:

6-[3-(4-benzamidopiperidino)-propoxy]-2-methyl-4H-1-benzopyran-4-one
7-{3-[4-(pyridino-3-carboxamido)-piperidino]-propoxy}-2-methyl-4H-1-benzopyran-4-one
7-{3-[4-(2-chlorobenzamido)-piperidino]-propoxy}-2-methyl-4H-1-benzopyran-4-one
7-[2-(4-benzamidopiperidino)-ethoxy]-2-methyl-4H-1-benzopyran-4-one
7-[4-(4-α-naphthoylaminopiperidino)-butoxy]-2-methyl-4H-1-benzopyran-4-one
7-[3-(4-trifluoroacetamidopiperidino)-propoxy]-2-methyl-4H-1-benzopyran-4-one.

The following Examples are given for the purpose of illustrating the present invention:

EXAMPLE 1

7-[3-(4-Benzamidopiperidino)-propoxy]-2-methyl-4H-1-benzopyran-4-one 5.3 g. (0.03 mol) 7-hydroxy-2-methyl-4H-1-benzopyran-4-one are added to a solution of 0.69 g. (0.03 mol) sodium in 75 ml. propan-2-ol and the mixture heated under reflux for 10 minutes. 8.4 g. (0.03 mol) 3-(4-Benzamidopiperidino)-propyl chloride dissolved in 25 ml. propan-2-ol are added thereto, the mixture heated under reflux for 12 hours, evaporated and the residue taken up in dichloromethane and the solution washed with dilute aqueous sodium hydroxide solution. The organic phase is evaporated and the residue recrystallised from propan-2-ol. There are obtained 6.8 g. (54% of theory) 7-[3-(4-benzamidopiperidino)propoxy]-2-methyl-4H-1-benzopyran-2-one; m.p. 173°–175° C.

EXAMPLE 2

The following compound is obtained in a manner analogous to that described in Example 1:

| designation | yield % | m.p. ° C. (solvent) |
|---|---|---|
| 5-[3-(4-benzamidopiperidino)-propoxy]-2-methyl-4H-1-benzopyran-2-one from 5-hydroxy-2-methyl-4H-1-benzopyran-4-one and 3-(4-benzamidopiperidino)-propyl chloride | 38 | 193–194 (propan-2-ol) |

EXAMPLE 3

7-[3-(4-Phenylacetamidopiperidino)-propoxy]-2-methyl-4H-1-benzopyran-4-one

A mixture of 5.94 g. (0.02 mol) 7-(3-bromopropoxy)-2-methyl-4H-1-benzopyran-4-one, 100 ml. tetrahydrofuran, 13 ml. triethylamine and 4.4 g. (0.02 mol) 4- phenylacetamidopiperidine is heated under reflux for 6 hours and then evaporated. The residue is mixed with water, extracted with dichloromethane, the extract evaporated and the residue recrystallised from propan-2-ol. There are obtained 5.0 g. (58% of theory) 7-[3-(4-phenylacetamidopiperidino)-propoxy]-2-methyl-4H-1-benzopyran-4-one; m.p. 172°–173° C.

EXAMPLE 4

The following compounds are obtained in a manner analogous to that described in Example 3:

| designation | yield % | m.p. ° C. (solvent) |
|---|---|---|
| (a) 7-[3-(4-acetamidopiperidino)-propoxy]-2-methyl-4H-1-benzopyran-4-one from 7-(3-bromopropoxy)-2-methyl-4H-1-benzopyran-4-one and 4-acetamidopiperidine | 39 | 165–167 (acetone) |
| (b) 7-{3-[4-(4-fluorobenzamido)-piperidino]-propoxy}-2-methyl-4H-1-benzopyran-4-one from 7-(3-bromopropoxy)-2-methyl-4H-1-benzopyran-4-one and 4-(4-fluorobenzamido)-piperidine | 59 | 188–189 (2-propanol) |
| (c) 7-{3-[4-(2-methylbenzamido)-piperidino]-propoxy}-2-methyl-4H-1-benzopyran-4-one from 7-(3-bromopropoxy)-2-methyl-4H-1-benzopyran-4-one and 4-(2-methylbenzamido)-piperidine | 45 | oxalate 205–207 (methanol/diethyl ether) |
| (d) 7-{3-[4-(2-methoxybenzamido)-piperidino]-propoxy}-2-methyl-4H-1-benzopyran-4-one from 7-(3-bromopropoxy)-2-methyl-4H-1-benzopyran-4-one and 4-(2-methoxybenzamido)-piperidine | 33 | oxalate 204–206 (ethanol) |
| (e) 7-{3-[4-(2-aminobenzamido)-piperidino]-propoxy}-2-methyl-4H-1-benzopyran-4-one from 7-(3-bromopropoxy)-2-methyl-4H-1-benzopyran-4-one and 4-(2-aminobenzamido)-piperidine | 35 | 154–157 (2-propanol) |
| (f) 7-{3-[4-(tetrahydrofuran-2-carboxamido)-piperidino]-propoxy}-2-methyl-4H-1-benzopyran-4-one from 7-(3-bromopropoxy)-2-methyl-4H-1-benzopyran-4-one and 4-(tetrahydrofuran-2-carboxamido)-piperidine | 21 | 105–107 (ethyl acetate/ligroin) |
| (g) 7-[3-(4-aminopiperidino)-propoxy]-2-methyl-4H-1-benzopyran-4-one from 7-(3-bromopropoxy)-2-methyl-4H-1-benzopyran-4-one and 4-aminopiperidine | 79 | 113–115 (dichloromethane) |

EXAMPLE 5

7-{3-[4-(2-Nitrobenzamido)-piperidino]-propoxy}-2-methyl-4H-1-benzopyran-4-one

A solution of 5.1 g. (0.027 mol) 2-nitrobenzoyl chloride in 25 ml. dichloromethane is added dropwise to a mixture of 6.95 g. (0.022 mol) 7-[3-(4-aminopiperidino)-propoxy]-2-methyl-4H-1-benzopyran-4-one (compound of Example 4g), 4.2 g. (0.05 mol) sodium hydrogen carbonate and 50 ml. dichloromethane. The reaction mixture is heated under reflux for 6 hours, then washed with water and evaporated. After recrystallisation of the residue from propan-2-ol, there are obtained 4.0 g. (40% of theory) 7-{3-[4-(2-nitrobenzamido)-piperidino]-propoxy}-2-methyl-4H-1-benzopyran-4-one; m.p. 185°–187° C.

EXAMPLE 6

The following compounds are obtained in a manner analogous to that described in Example 5:

| designation | Yield % | m.p. ° C. (solvent) |
|---|---|---|
| (a) 7-[3-(4-cyclopropanecarboxamido-piperidino)-propoxy]-2-methyl-4H-1-benzopyran-4-one from 7-[3-(4-aminopiperidino)-propoxy]-2-methyl-4H-1-benzopyran-4-one and cyclopropanecarbonyl chloride | 30 | 170–172 (ethyl acetate) |
| (b) 7-{3-[4-(thiophene-2-carboxamido)-piperidino]-propoxy}-2-methyl-4H-1-benzopyran-4-one from 7-[3-(4-aminopiperidino)-propoxy]-2-methyl-4H-1-benzopyran-4-one and thiophene-2-carbonyl chloride | 38 | 178–180 (dichloromethane/methanol) |

EXAMPLE 7

7-{3-[4-(2-Hydroxybenzamido)-piperidino]-propoxy}-2-methyl-4H-1-benzopyran-4-one A mixture of 4.9 g. (0.02 mol) 4-(2-acetoxybenzamido)-piperidine, 5.6 g. (0.02 mol) 7-(3-bromopropoxy)-2-methyl-4H-1-benzopyran-4-one, 13.9 ml. (0.10 mol) triethylamine and 100 ml. tetrahydrofuran is heated under reflux for 10 hours and then evaporated. The 7-{3-[4-(2-acetoxybenzamido)-piperidino]-propoxy}-2-methyl-4H-1-benzopyran-4-one obtained as a crude product is mixed with 100 ml. 1 N aqueous sodium hydroxide solution, stirred for 1 hour, filtered, washed with ethyl acetate and the aqueous phase then neutralised. The precipitate obtained is taken up in acetone, mixed with excess ethereal hydrochloric acid and the dihydrochloride of the desired end product isolated; m.p. 169°–170° C. The yield is 4.6 g. (45% of theory).

EXAMPLE 8

Tablets are prepared, each of which contains 10 mg. 7-[3-(4-benzamidopiperidino)-propoxy]-2-methyl-4H-1-benzopyran-4-one. The tablets are prepared according to the following formulation:

| | |
|---|---|
| 7-8 3-(4-benzamidopiperidino)-propoxy]-2-methyl-4H-1-benzopyran-4-one | 10 g. |
| lactose | 80 g. |
| starch | 29 g. |
| magnesium stearate | 1 g. |

The above active compound is finely pulverised and mixed with the lactose and starch. The mixture thus obtained is then granulated in conventional manner. The magnesium stearate is added to the granulate and the mixture pressed to give 1000 tablets, each having a weight of 0.12 g.

The following tests were conducted to determine the effectiveness of the new compounds in the inhibition of antigen induced bronchospasm in passively sensitized guinea pigs.

These tests were carried out as follows:

Preparation of Antiserum

The antigen is twice recrystallised egg albumin. Equal volumes of saline solution of antigen (5 mg/ml) and Freund's complete adjuvant were emulsified and 0.15 ml injected into each hind foot of adult male guinea pigs (DAVIES and JOHNSON: Int. Arch. Allergy 41, 648-654 (1971)).

The animals were bled and the pooled serum stored at −20° C.

Passive sensitization

Injections of 0.5 ml antiserum of 1:50 dilution were given i.v. 24–48 h before challenge.

Guinea pigs were anaesthetized with pentobarbitone sodium (40 mg/kg i.p.). Cannulae were tied into the trachea and the jugular vein and the lung inflated with a pump at a rate of 72 strokes/min and a constant stroke volume of 6–8 ml.

Bronchospasm, provoked by injecting ovalbumin i.v. was measured as described in COLLIER, H. O. J., J. A. HOLGATE, M. SCHACHTER: THE BRONCHOCONSTRICTOR ACTION OF BRADYKININ IN THE GUINEA-PIG. Brit. J. Pharmacol. 15, 290 (1960) and KONZETT, H. und R. RÖSSLER: Versuchsanordnung zu Untersuchungen an der Bronchialmuskulatur. Naunyn-Schmiedebergs Arch. exp. Path. Pharmk. 195, 71–74 (1940)

Drugs were applied p.o. 60 min before antigen. For calculation the following formular was used:

$$\% \text{ Bronchospasm } \frac{b-a}{m-a} \times 100$$

b = Bronchospasm after antigen injection, measured in mm from tracing m = maximum height of tracing in mm with arm of the trachea-cannula clamped a = pre injection height of the tracing in mm % inhibition of bronchospasm was calculated by comparing control groups with drug pretreated groups 3 min after antigen application.

TABLE

Inhibition of Bronchospasm (BrSp) In Passively Sensitized Guinea Pigs

| Test Compound | Dose mg/kg p.o. | % Inhibition of BrSp |
|---|---|---|
| 3,4-Dimethyl-7-{3-[4-(thiophene-2-carboxamido)-piperidino]-propoxy}-cumarin | 0.75<br>1.5<br>3.0 | 0<br>40<br>67 |
| 7-[3-(4-Benzamido-piperidino)-propoxy]-2-methyl-4H-1-benzopyran-4-one | 0.38<br>0.75 | 55<br>64 |
| 7-{3-[4-(4-fluorobenzamido)-piperidino]-propoxy}-2-methyl-4H-1-benzopyran-4-one | 0.38 | 46 |
| 7-{3-[4-(2-methylbenzamido)-piperidino]-propoxy}-2-methyl-4H-1-benzopyran-4-one | 0.75 | 60 |

It will be understood that the specification and examples are illustrative but not limitative of the present invention and that other embodiments within the spirit and scope of the invention will suggest themselves to those skilled in the art.

What is claimed is:

1. Benzopyranyl ether compound of the formula

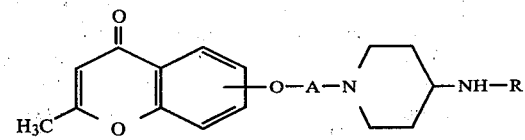

wherein

A is alkylene or 2 to 4 carbons; and

R is hydrogen or acyl selected from the group consisting of substituted or unsubstituted alkanoyl radicals containing up to 5 carbon atoms, wherein the substituents are selected from fluorine, chlorine, bromine, phenyl or naphthyl;

substituted or unsubstituted lower alkenoyl radicals containing 3 to 6 carbon atoms, wherein the substituents are selected from substituted or unsubstituted phenyl wherein the substituents are selected from hydroxyl, halogen, alkyl containing up to 6 carbon atoms and alkoxy containing up to 6 carbon atoms unsubstituted or substituted benzoyl, or naphthoyl wherein the substituents are fluorine, chlorine, bromine, hydroxyl, lower alkyl, lower alkoxy, lower alkoxycarbonyl, lower alkanoyloxy, carboxyl, nitro, amino, lower alkanoylamino, nitrile, trifluoromethyl, carbamoyl, lower alkylthio, lower alkylsulphinyl, lower alkylsulphonyl, lower alkanoyl, benzoyl, hydroxy lower alkyl or lower alkoxy lower alkyl;

furancarbonyl, thiophenecarbonyl, pyridinecarbonyl, tetrahydrofuran-carbonyl, tetrahydrothiophene-carbonyl or $C_3$–$C_7$ cycloalkylcarbonyl; or benzene-sulphonyl or methane sulphonyl, and salts thereof with pharmacologically acceptable acids.

2. Benzopyranyl ether compound as claimed in claim 1, wherein A is ethylene.

3. Benzopyranyl ether compound as claimed in claim 1, wherein A is propylene.

4. Benzopyranyl ether compound as claimed in claim 1, wherein A is butylene.

5. Benzopyranyl ether compound as claimed in claim 1, wherein R is hydrogen.

6. Benzopyranyl ether compound as claimed in claim 1 wherein R is benzoyl or benzoyl substituted by fluorine, chlorine, methyl, methoxy, hydroxy, amino or nitro.

7. Benzopyranyl ether compound as claimed in claim 1, wherein R is alkanoyl with up to 5 carbon atoms.

8. Benzopyranyl ether compound as claimed in claim 1, designated 7-[3-(4-Benzamidopiperidino)-propoxy]-2-methyl-4H-1-benzopyran-4-one.

9. Benzopyranyl ether compound as claimed in claim 1, designated 7-{3-[4-(4-fluorobenzamido)-piperidino]-propoxy}-2-methyl-4H-1-benzopyran-4-one.

10. Benzopyranyl ether compound as claimed in claim 1, designated 7-{3-[4-(2-methylbenzamido)-piperidino]-propoxy}-2-methyl-4H-1-benzopyran-4-one.

11. Pharmaceutical composition for the treatment of allergic diseases comprising a pharmaceutical acceptable carrier and, in an amount effective to treat allergic diseases, at least one benzopyranyl ether compound as claimed in claim 1.

12. Pharmaceutical composition as claimed in claim 11, wherein said benzopyranyl ether compound is at least one of the following:

- 7-[3-(4-Benzamidopiperidino)-propoxy]-2-methyl-4H-benzopyran-4-one;
- 7-{3-[4-(4-fluorobenzamido)-piperidino]-propoxy}-2-methyl-4H-1-benzopyran-4-one; and
- 7-{3-[4-(2-methylbenzamido)-piperidino]-propoxy}-2-methyl-4H-1-benzopyran-4-one.

13. Method of treatment of allergic diseases which comprises applying to an afflicted subject an effective amount of a benzopyranyl ether compound as claimed in claim 1.

14. Method of treatment of allergic diseases as claimed in claim 13, wherein said benzopyranyll ether is at least one compound selected from

- 7-[3-(4-Benzamidopiperidino)-propoxy]-2-methyl-4H-benzopyran-4-one;
- 7-{3-[4-(4-fluorobenzamido)-piperidino]-propoxy}-2-methyl-4H-1-benzopyran-4-one; and
- 7-{3-[4-(2-methylbenzamido)-piperidino]-propoxy}-2-methyl-4H-1-benzopyran-4-one.

15. Method of treatment of allergic diseases as claimed in claim 13, wherein said compound is applied in an amount of from 0.1 to 50 mg/kg of body weight of the subject, per day.

16. Method of treatment of allergic diseases as claimed in claim 15, wherein the applied dosage is 0.5 to 40 mg/kg.

17. Method of treatment of allergic diseases as claimed in claim 16, wherein the applied dosage is 1 to 20 mg/kg.

* * * * *